United States Patent [19]

Ichijo et al.

[11] Patent Number: 5,229,495

[45] Date of Patent: Jul. 20, 1993

[54] SUBSTANTIALLY PURE RECEPTOR LIKE TGF-β1 BINDING MOLECULES AND USES THEREOF

[75] Inventors: Hidenori Ichijo; Kohei Miyazono; Lars Rönnstrand; Ulf Hellman; Christer Wernstedt; Carl-Henrik Heldin, all of Upsala, Sweden

[73] Assignee: Ludwig Institute for Cancer Research, New York, N.Y.

[21] Appl. No.: 717,316

[22] Filed: Jun. 18, 1991

[51] Int. Cl.⁵ .................... C07K 15/08; G01N 33/567
[52] U.S. Cl. .................................. 530/350; 436/503; 530/395
[58] Field of Search ...................... 530/350, 351, 395; 436/503, 504

[56] References Cited

FOREIGN PATENT DOCUMENTS

WO9113152  9/1991  PCT Int'l Appl. .

OTHER PUBLICATIONS

Miyazono et al., Nature 338 (6211): 158–160 (Mar. 9, 1989).
Miyazono et al., J. Biol. Chem. 263 (13): 6407–6415 (1988).
Kanzaki et al., Cell 61: 1051–1061 (Jun. 15, 1990).
Wakefield et al., J. Biol. Chem. 263(16); 7646–7654 (1988).

Primary Examiner—Jeffrey E. Russel
Attorney, Agent, or Firm—Felfe & Lynch

[57] ABSTRACT

The invention relates to a family of substantially pure, receptor like TGF-β1 binding glycoproteins. These molecules are characterized by molecular masses of 160 kd, 70–80 kd, and 30–40 kd as determined by SDS-PAGE, and the ability to bind the TGF-β1 molecule. This family of molecules is useful in identifying and/or quantifying TGF-β1 in a sample, as well as inhibiting its effect on cells.

5 Claims, 11 Drawing Sheets

FIG. 11 kDa

200-

93-

69-

46-

◀ 36

30-

14-

SUBSTANTIALLY PURE RECEPTOR LIKE TGF-β1 BINDING MOLECULES AND USES THEREOF

FIELD OF THE INVENTION

This invention relates to protein biochemistry. More particularly, it relates to molecules which bind to the substance known as transforming growth factor-β1 ("TGF-β1" hereafter).

BACKGROUND AND PRIOR ART

A family of molecules is referred to as the "TGF-βs". These are 25 kd dimeric proteins which have multifunctional effects on growth and differentiation of cells, both in vitro and in vivo. See Roberts et al. in Peptide Growth Factors And Their Receptors I (Sporn et al., eds., pp 419–472; Springer-Verlag, Berlin, 1990); Moses et al., Cell 63: 245–247 (1990); Massagué, Ann. Rev. Cell. Biol. 6: 597–641 (1990). The family contains at least three different, structurally related members, identified as "β1, β2 and β3". Many other proteins are more distantly related, including bone morphogenic proteins, Mëllerian inhibitory substance, activins, inhibins, and so forth.

Originally, the TGF-β family of proteins was identified as being involved in increasing anchorage independent growth of normal rat kidney cells; however, the proteins are also recognized as a potent growth inhibitor for diverse cell types, including hematopoietic cells, lymphocytes, epithelial and endothelial cells (Ohta et al., Nature 329: 539–541 (1987); Kehri et al., J. Immunol 137: 3855–3860 (1986); Moses et al., in Cancer Cel)s 3 (Feramisco et al., ed; Cold Spring Harbor, N.Y., 1985); pg. 65–71; Baird et al.. Biochem. Biophys Res Commun 138 476–482 (1986); FraterSchröder et al., Biochem. Biophys. Res. Commun. 137: 295–302 (1986); Heimark et al., Science 233: 1078–1080 (1986)). The molecules have a dramatic effect on accumulation of extracellular matrix proteins (Massagué, supra), and have been implicated in pathogenesis glomerulonephritis (Border et al., Nature 346: 371–374 (1990)); liver cirrhosis (Castilla et al., N. Eng. J. Med. 324: 933–940 (1990)); and pulmonary fibrosis (Khalil et al., in Clinical Application of TGF-β1 (Bock et al., ed. Ciba Foundation Symposium 157, John Willy & Sons, 1991, pg. 194–211).

The TGF-β family interacts with other proteins on several levels. One of these is mediation of binding via cell surface receptors. The art recognizes three distinct high affinity receptors for TGF-βs, referred to as types I, II and III. The first two of these have molecular masses of 53 and 70–85 kd, respectively, while the third is denoted "betaglycan" because of its proteoglycan like structure, and is further characterized by a molecular mass of 200–400 kd. Massagué et al., in Transforming Growth Factor-βs: Chemistry, Biology and Therapeutics (Piez et al., eds., Ann. N.Y. Acad. Sci. 593, 1990), pg. 59–72; Segarini et al., in Clinical Applications of TGF-β (Bock et al., eds. Ciba Foundation Symposium 157, John Wiley & Sons, 1991, pp. 29–50). The betaglycan molecule is a membrane proteoglycan, having a 100–140 kd core protein with unknown functional importance, while type I and II receptors appear to be involved in transduction of TGF-β cellular effect. Segarini et al., J. Biol. Chem. 263: 8366–8370 (1988); Cheifetz et al., J. Biol. Chem. 263: 16884–16991 (1988); Massagué et al., supra. Some cell lines express only type I receptors and are inhibited by TGF-β1. These include hematopoietic progenitor cell lines (Ohta et al., supra) and squamous cancer cell lines (Ichiyo et al., Exp. Cell Res. 187: 263–269 (1990)). Mutant cell lines of mink epithelial cells have been shown to have lost or to have anomalous expression of type I and/or type II receptors (Boyd et al., J. Biol. Chem. 264: 2272–2278 (1989); Laiho et al., J. Biol. Chem. 265: 18518–18524 (1990)).

Additional binding molecules for TGF-β having molecular masses of 60 kd, 85–320 kd, and 400 kd have been reported in pituitary tumor cell lines, rat glomeruli, and bovine liver cells, respectively, as reported by Cheifetz et al., J. Biol. Chem. 263: 17225–17228 (1988); Mackay et al., J. Biol. Chem. 265: 9351–9356 (1990); O'Grady et al., J. Biol. Chem. 266: 8583–8589 (1991).

On another level, the precursors of TGF-β, especially TGF-β1, interact with protein molecules known as the latent TGF-binding protein or "LTBP". The interaction yields a high molecular weight, inactive complex which is secreted from the cell. This is sometimes referred to as the latent TGF-β1 complex. See Miyazono et al., J. Biol. Chem. 263: 6407–6415 (1988); pircher et al., Biochem. Biophys. Res. Commun. 136: 30–37 (1984); Wakefield et al., J. Cell Biol. 105: 965–975 (1987). The inactive or latent complexes contain a noncovalent association of TGF-β1, a disulphide bonded complex of a dimer of N-terminal peptide of TGF-β1 precursor and as third component, the LTBP. This third component occurs as a molecule with a molecular mass which may range from 125–190 kds. Experiments have shown that the binding proteins do not inactivate TGF-β1.

The molecules discussed supra are sometimes referred to as "binding proteins", because they do, in fact bind to the TGF-β1 precursor. A fundamental difference between these molecules and the molecules of the invention is that while the prior art molecules may be referred to as "synthesis" binders, it is more appropriate to describe the invention as involving "effector" binders. The synthesis binders are involved in the "packaging" of TGF-β1 in the cell, such that it is released for subsequent activities. When bound to the prior art molecules, TGFs are essentially inert. In contrast, the protein containing molecules of the invention may be seen as "effectors" in that TGF-β1 binds directly to these, so as to effect a response thereby. This distinction should be kept in mind in connection with this application.

It is an object of the invention to describe these substantially pure, receptor like TGF-β1 binding protein containing molecules, which are characterized by molecular masses of 160 kd, 70–80 kd, and 35–40 kd as determined by SDS-PAGE, as well as their uses in various processes. The ranges are due to the behavior of the species under reducing and non-reducing conditions, as will be seen infra.

The objects of the invention discussed supra as well as others will be seen from the disclosure which follows.

BRIEF DESCRIPTION OF THE FIGURES

FIG. 11 shows in gel binding of the 40 kd receptor like binding protein.

DETAILED DESCRIPTION OF PREFERRED EMBODIMENTS

Example 1

Figure 1:
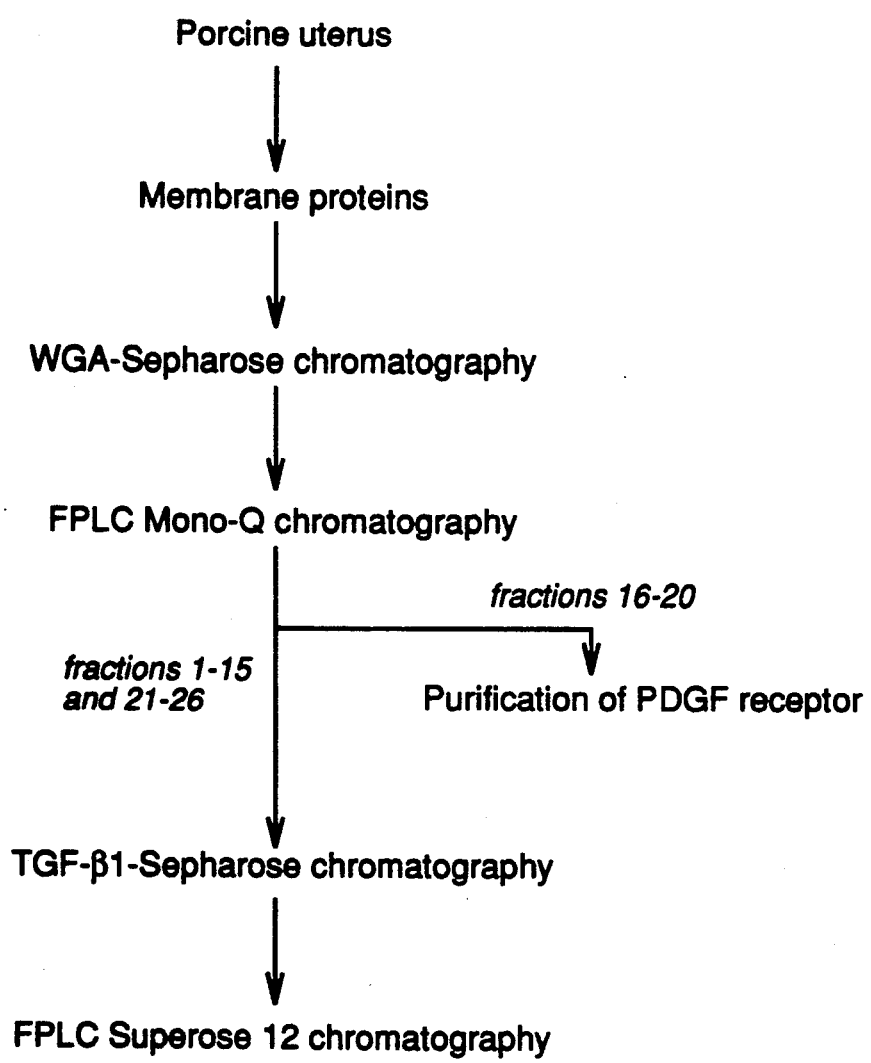
FIG. 1 provides a schematic outline of the purification protocol used to isolate the substantially pure receptor like transforming growth factor β1 binding proteins of the invention.
Figure 2:
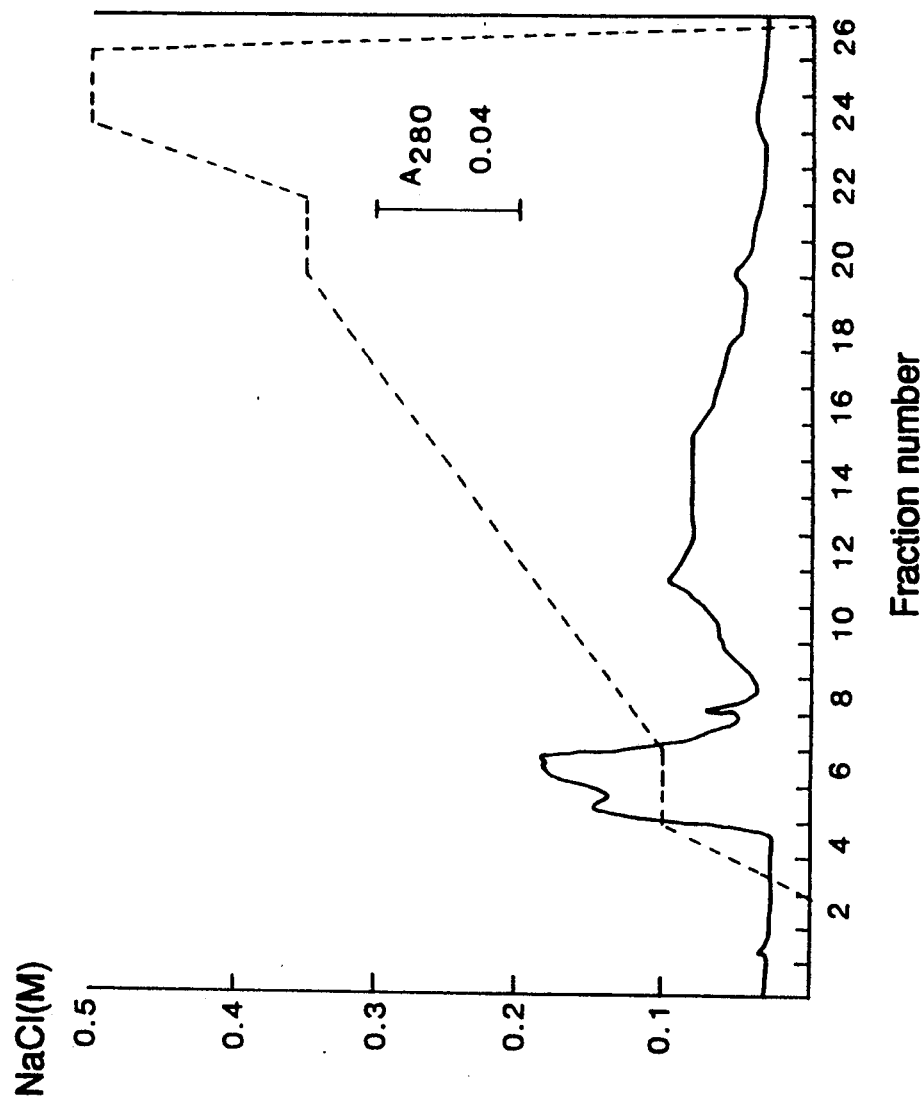
FIG. 2 shows a protein profile of a representative FPLC run for the binding proteins of the invention.

A protocol originally described by Rönnstrand et al., J. Biol. Chem. 262: 2929-2932 (1987) for purifying PDGF receptor was followed. Briefly, porcine uterus tissue was used as starting material for preparation of membranes. Differential centrifugation following Rönnstrand, supra, was used to obtain the membranes. The membrane proteins were then solubilized in Triton X-100 ®, and subjected to chromatography on wheat germ agglutinin Sepharose and fast protein liquid chromatography Mono-Q columns First, the proteins were purified on the wheat germ agglutinin column, and the purified material was then applied to an FPLC Mono Q column, using increasing concentrations of NaCl. Twenty-six fractions were taken from the column. Of these, fractions 16-20 were pooled and used to purify PDGF receptor; the other fractions were stored at −20° C. and used as starting material to purify the receptor like binding proteins of the invention. FIG. 2 shows the concentration of NaCl used for each fraction, via the dotted line. Fractions 16-20 were used for PDGF purification.

Example 2

To remove the receptor like binding proteins from the fractions obtained following Example 1, a TGF-β1 Sepharose column was prepared. This was accomplished using recombinant TGF-β1 purified from conditioned medium of CHO cells, transfected with human TGF-β1 cDNA. One mg of TGF-β1 was coupled to 0.5 g of cyanogen bromide activated Sepharose 4B, to yield about 0.67 mg of TGF-β1/ml of gel.

Following preparation of the column, fractions 1-15 and 21-26 from example 1 were thawed, pooled, and dialyzed against binding buffer (0.2% Triton X-100 ®, 125 mM NaCl, 5 mM KCl, 5mM MgSO$_4$, 1.2 mM CaCl$_2$, 20 mM HEPES, pH 7.4). Twenty-five ml amounts of dialyzed sample were then mixed with 2.5 ml of the previously prepared Sepharose beads, and the resulting suspension was incubated overnight at 4° C, with gentle shaking The beads were then collected in a column which was then washed with 25 ml of binding buffer, and then 25 ml of binding buffer with 500 mM NaCl. Bound molecules were then eluted with 5 ml of a solution of 0.2% Triton X-100 ®, 500 mM NaCl, in 100 mM sodium acetate buffer, pH 5.5, followed by 5 ml of 0.2% Triton X-100 ®, 500 mM NaCl, and 100 mM acetic acid at pH 3.5, to yield what will be referred to as the "pH 3.5 eluate" hereafter.

Example 3

The pH 3.5 eluate fractions from four to six chromatography runs, as discussed supra, were pooled and mixed with four volumes of acetone. The protein portion was precipitated at −20° C. for 60 minutes, followed by centrifugation at 17,000xg at 4° C. for 20 minutes. The resulting protein pellets were dried, resuspended in 500 ul of 70% formic acid, followed by application to an FPLC Superose 12 column which had been pre-equilibrated and eluted with 70% formic acid at a flow rate of 0.5 ml/min. Fractions (250 ul) were collected, and aliquots of individual fractions were lyophilized and subjected to further analysis.

Example 4

Fractions obtained following example 2 were examined for $^{125}$I- TGF-β1 binding, using affinity cross linking and "in gel" binding procedures.

To do this, 50 ul portions of the individual Mono-Q fractions were incubated for three hours at 4° C. in the presence of 1 nM of recombinant TGF-β1 labeled with $^{125}$I following Frolik et al., J. Biol. Chem. 259: 10995-11000 (1984), to yield a product with $5 \times 10^6$ cpm/ml. The incubation took place with fractions that either had been dialyzed against the binding buffer described supra, or dissolved in it.

Figure 3:
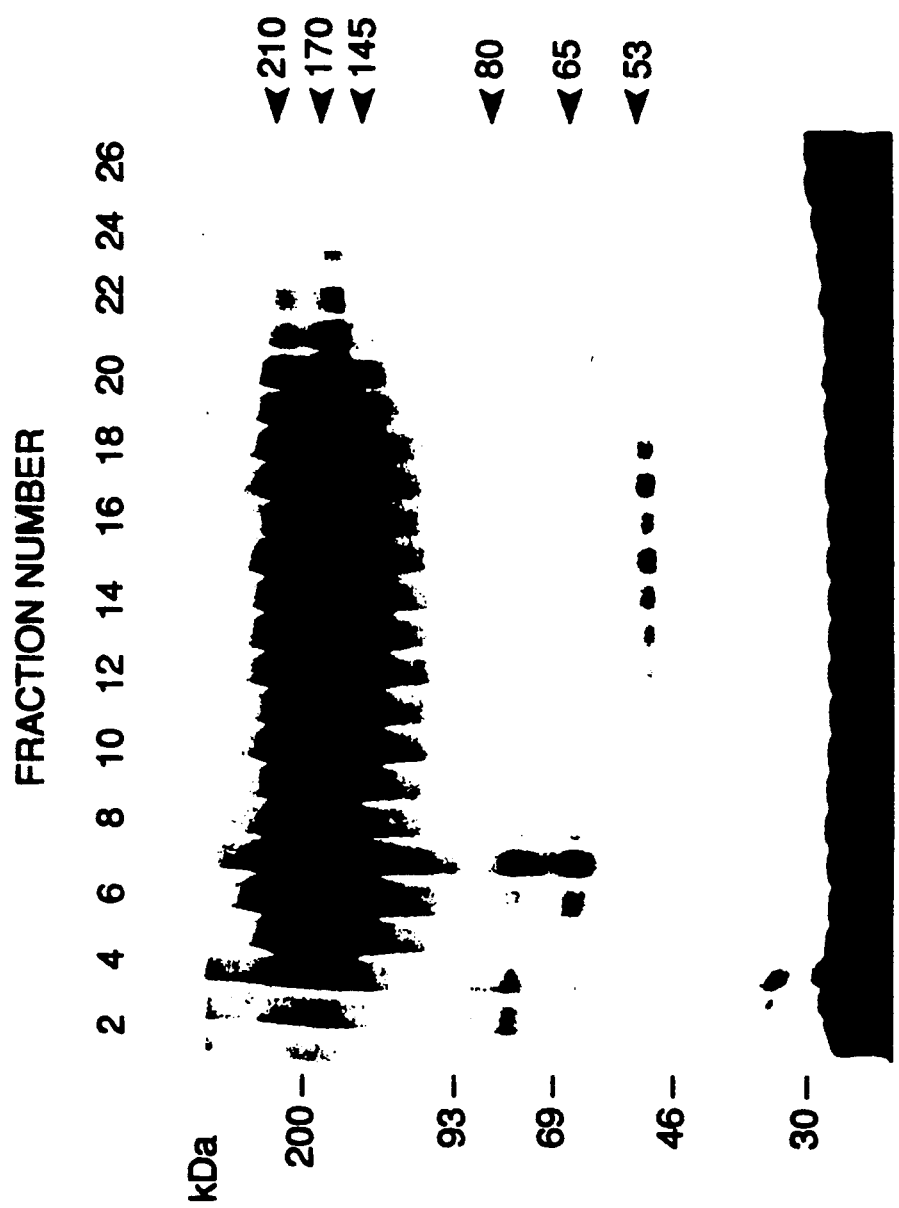
FIG. 3 shows SDS gel runs for various fractions prepared according to the invention, following affinity cross linking with $^{125}$I-TGF-β1.

The affinity labeled proteins were then cross-linked using 0.14 mM of disuccinimidyl suberate ("DSS") for 15 minutes at 4° C. The cross-linking reaction was quenched by adding SDS-electrophoresis sample buffer containing 80 mM Tris. In this and in following examples, the samples were then heated at 95° C. for three minutes in SDS-sample buffer which did or did not contain 10 mM dithiothreitol (DTT). The samples were then applied to 5-15% SDS-polyacrylamide gels following Blobel et al., J. Cell Biol. 67: 835-851 (1975) for electrophoresis, under either reducing or non-reducing conditions. Gels were then fixed in 25% methanol, 7.5% acetic acid, and dried and subjected to 12-days of autoradiography using Fuji X-ray film The results of the autoradiography are shown in FIG. 3.

Example 5

Figure 4:
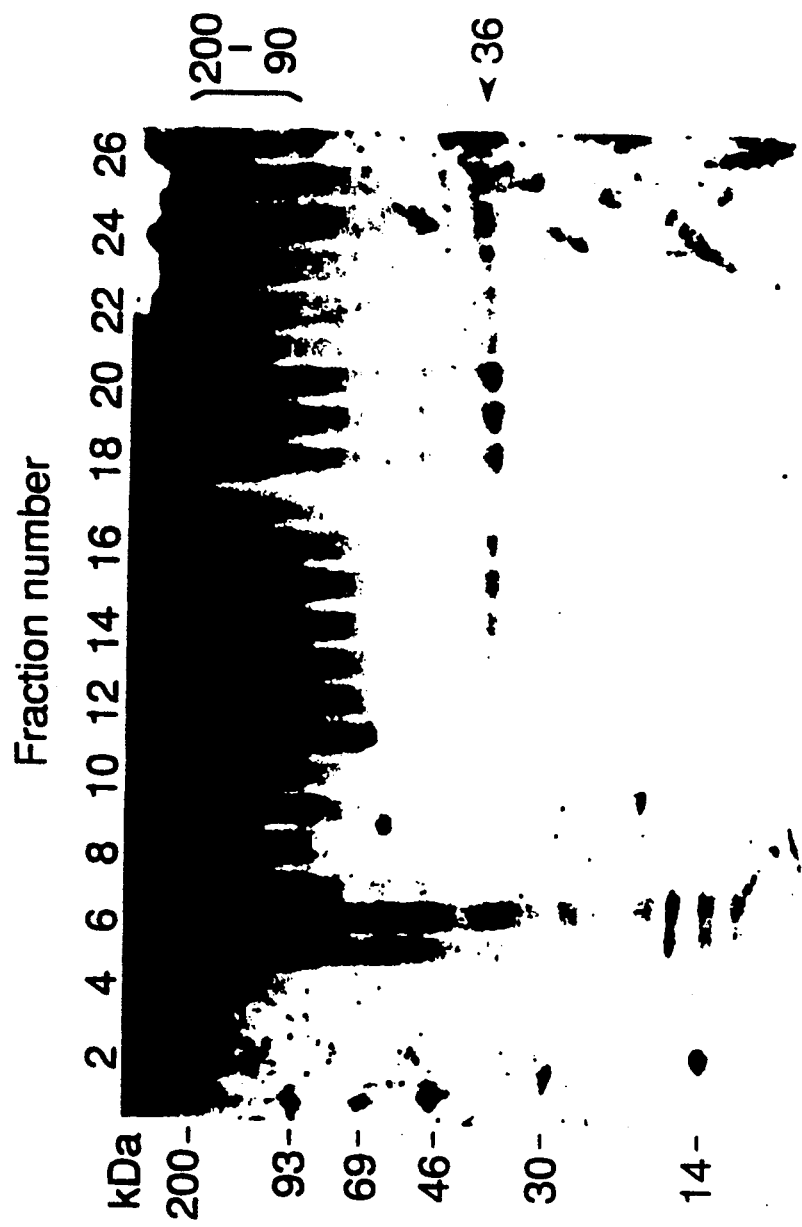
FIG. 4 depicts "in-gel" ligand binding of fractions following FPLC Mono-Q chromatography.

Experiments were also carried out to study "in gel" binding using radiolabeled TGF-β1. To do this, the method described by Murphy et al., Anal. Biochem. 187: 197-201 (1990) for $^{125}$I heparin, was used with some minor modifications. To summarize, 250 ul of individual fractions were lyophilized and subjected to non-reducing SDS gel electrophoresis. Following SDS-gel electrophoresis, gels were fixed for 30 minutes in 40% methanol, 7% acetic acid, and rinsed several times with distilled water. The gels were then incubated overnight with 10% ethanol, 10 mM Tris-HCl, pH 7.5 at 4° C. with gentle shaking, followed by washing for one hour with the same buffer. The gels were then incubated for 30 minutes with binding buffer containing bovine serum albumin (BSA) at 2 mg/ml. Gels were then transferred to plastic bags with 10 ml binding buffer containing $1 \times 10^6$ cpm of $^{125}$I-TGF-β1 and 2 mg/ml of BSA. These bags were sealed and shaken overnight at 4° C. Excess $^{125}$I-TGF-$\beta$1 was removed, and the gels were then washed with 500 ml of binding buffer for 30 minutes, followed by two washes with 500 mM binding buffer containing 400 mM NaCl. Each wash was for 30 minutes. Following this, gels were dried and subjected to autoradiography as per example 4, but for three days. FIG. 4 shows these results.

In both of examples 4 and 5, $^{14}$C labeled molecular weight markers were used as follows: myosin (200 kd), phosphorylase B (92.5 kd) bovine serum albumin (69 kd), ovalbumin (46 kd), carbonic anhydrase (30 kd), lysozyme (14.3 kd).

The results from example 4 showed complexes of apparent molecular masses of 210,000; 170,000; and 145,000 kd from most of the fractions, as well as complexes with molecular masses of 80,000 and 65,000 in fractions 2-10, plus one of 53,000 in fractions 10-20. Example 5 (FIG. 4) results showed several binding components in the 90-200 kd range in fractions 5-26, plus a prominent band of 36 kd in fractions 11-26.

Example 6

The results obtained in Example 5 gave a pattern which was similar to that observed by Seganini et al., J. Biol. Chem. 263: 8366-8370 (1988), and Cheifetz et al., J. Biol. Chem. 263: 16884-16991 (1988), for betaglycan affinity labeled with $^{125}$I-TGF-$\beta$1. To determine whether either of the 210 kd or 170 kd components represented betaglycan, samples were again cross linked with $^{125}$I-TGF-$\beta$1, and digested with heparinase and chondroitinase. The references cited to supra had shown that the proteoglycan betaglycan shifts to 100-140 kd following such treatments. The 210 and 170 kd complexes tested herein showed no such movement, strongly suggesting that they did not represent betaglycan.

Example 7

Once it had been shown that there was binding activity for the proteins of examples 1-6, further purification steps were carried out.

Again referring to the fraction obtained with the Mono-Q column, all but fractions 16-20 were combined and dialyzed against dialysis buffer as described supra. Again, following the protocols described supra the dialyzed material was subjected to affinity chromatography using immobilized TGF-$\beta$1. Following this, the column was washed with binding buffer, described supra, then with binding buffer at higher ionic strength, i.e., 0.5M NaCl. Following this, two elutions were carried out, first with an elution buffer at pH 5.5, and than at pH 3.5 Each fraction was analyzed on SDS-PAGE, using silver staining in the absence and presence of reducing agent.

Figure 5:
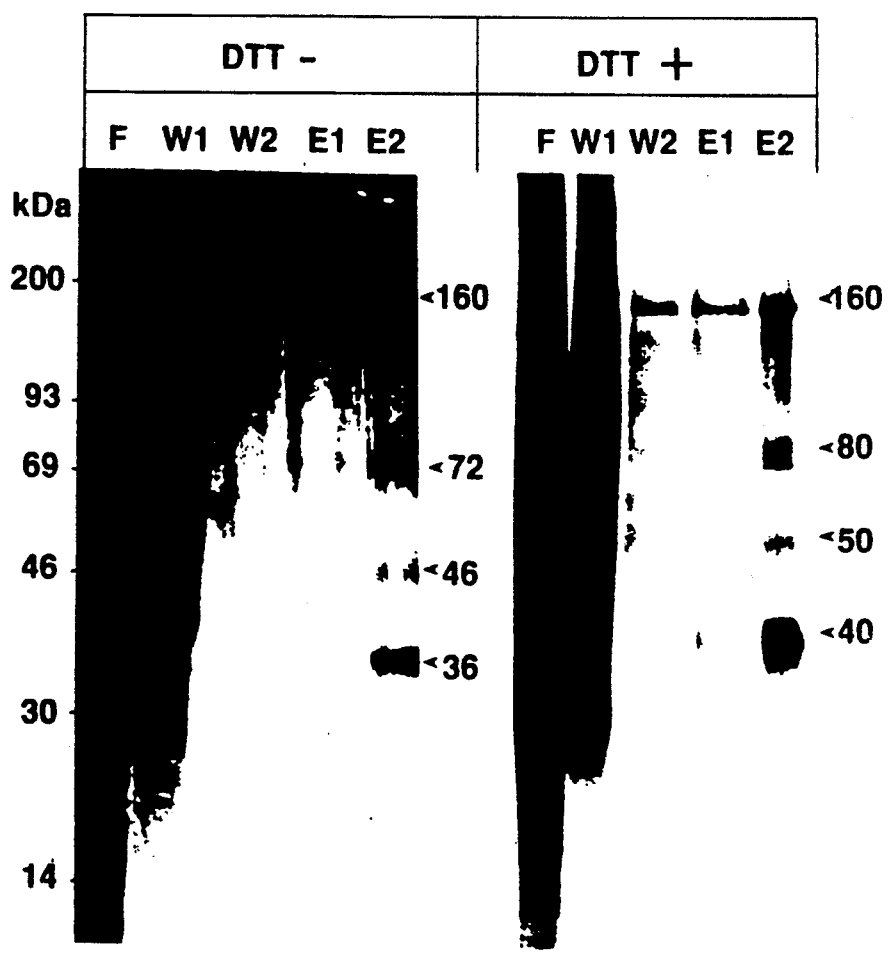
FIG. 5 shows SDS-gel electrophoretic analysis of fractions obtained following sepharose chromatography using TGF-β1.

The results from these different fractionations are shown in FIG. 5, where "FT" refers to the flow through material, "W1" to the low ionic strength wash, "W2" to the high ionic strength wash, "E1" to the elution at pH 5.5, and E2 to the elution at pH 3.5. Very little protein eluted at pH 5.5, while at pH 3.5 and under non reducing conditions, materials eluted which showed apparent molecular masses of 160, 72, 46 and 36 kilodaltons. When this fraction was tested under reducing conditions, species of apparent molecular masses of 160, 80, 50 and 40 kilodaltons were observed. This suggests that four separate species were present, having molecular weights of 160 kd, and ranging from 70-80 kd, 45-50 kd, and 35-40 kd.

Example 8

Figure 6:
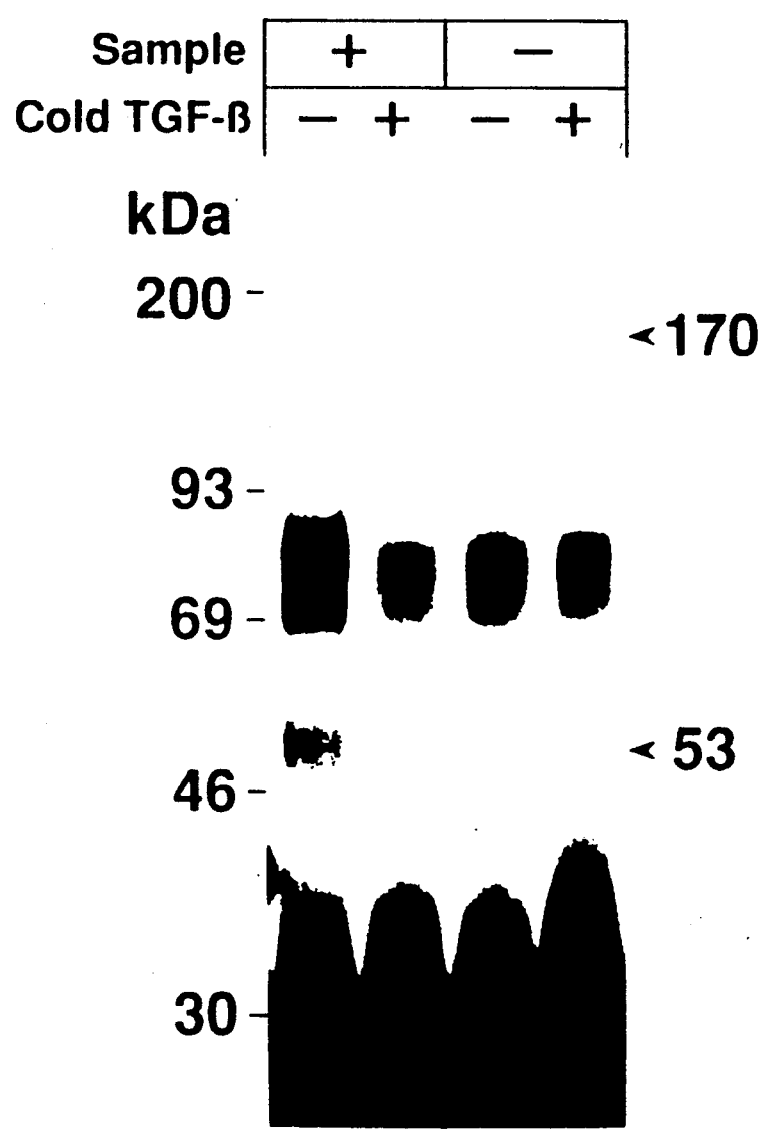
FIG. 6 presents analysis of the pH 3.5 elution fraction of TGF-β1 Sepharose chromatography, following affinity labelling using $^{125}$I-TGF-β1.

The pH 3.5 eluate clearly contained the material of interest, and was subjected to further analysis. An aliquot of the fraction was lyophilized, redissolved in binding buffer, and incubated with 1 nM $^{125}$I-TGF-$\beta$1, prepared as described supra, either without or with an excess amount of unlabeled TGF-$\beta$1 (400 nM). Again, following the protocols set forth supra, these materials were cross linked with DSS and analyzed via SDS gel electrophoresis under reducing conditions. Radiographic data from these experiments are presented in FIG. 6, and show complexes with apparent molecular weights of 170 and 53 kd. These complexes were associated with $^{125}$I-TGF-$\beta$1. This radiolabelled molecule has a molecular weight of 12.5 kd under reduced conditions, so it would appear that the binding materials are the 160 and 40 kd species of Example 7. Components of molecular mass 70-90 kd and 25 kd were also found, but there was no observed displacement even when 400 fold cold molar excesses of unlabeled TGF-$\beta$1 were used. Also, these bands were found in control lanes where samples were not present, suggesting free $^{125}$I-TGF-$\beta$1 and the labeled molecule non-specifically cross linked to BSA.

Example 9

Figure 7:
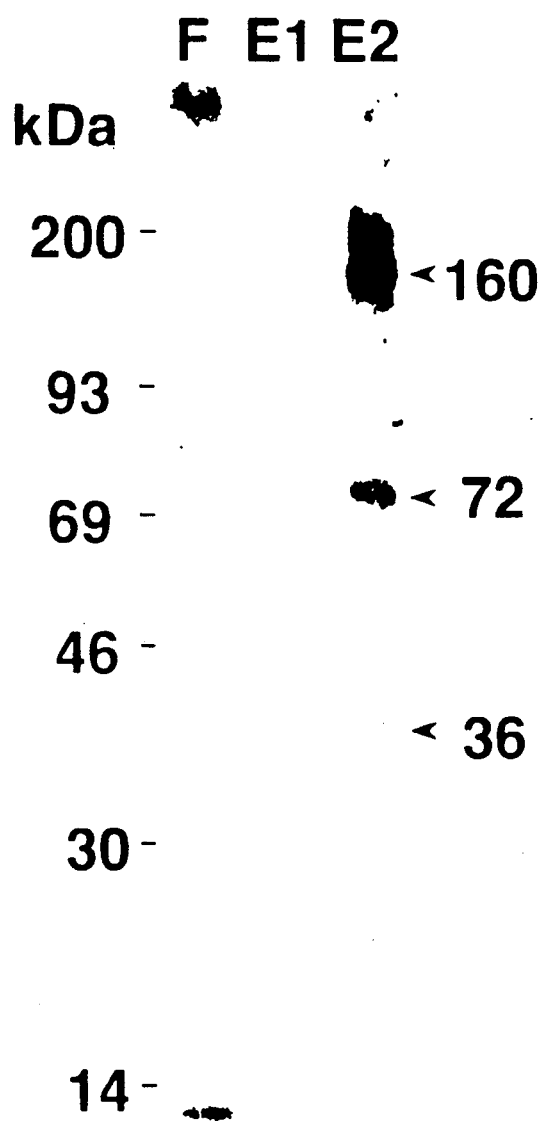
FIG. 7 presents an analysis of different TGF-β1 Sepharose chromatography fractions using "in-gel" ligand binding.

The pH 3.5 fraction was then used for "in gel" ligand binding, as were some of the other fractions. Specifically, 70 ul of FT, E1 and E2 fractions were subjected to the same protocol for in gel ligand binding as described previously. FIG. 7 shows these results. Two of the three components recognized were identical to components found using the affinity labeling experiment of Example 8. A third, an 80 kd band, may have been hidden in the diffuse 70-90 kd band shown in FIG. 6 and discussed in Example 8. A fourth component, a 50 kd band, was the material present in lowest quantity in the pH 3.5 fraction.

Example 10

The foregoing examples showed that there were several receptor like binding proteins present. In order to separate these, a size separation method was used. Specifically, pH 3.5 eluates from four to six TGF-$\beta$1 Sepharose chromatographies were pooled and subjected to acetone precipitation, as per Example 2, supra. Precipitates were dried, redissolved in 70% formic acid, and applied to an FPLC Superose 12 column eluted in 70% formic acid.

Figure 8:
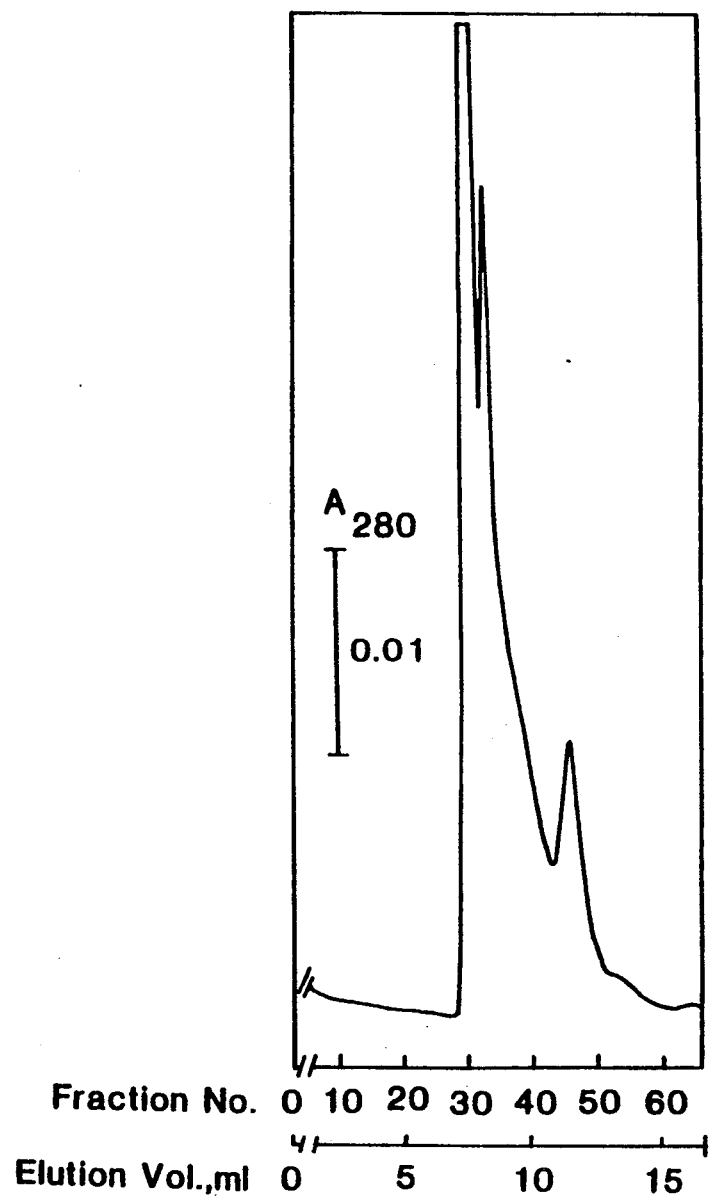
FIG. 8 is a protein profile of a chromatogram of the pH 3.5 elution fraction, following acetone precipitation concentration.

The protein profile of this chromatography is shown in FIG. 8, where three major protein peaks were found at fractions 28-31, 32-34, and 44-48. A shoulder was found at fractions 36-40.

Figure 9:
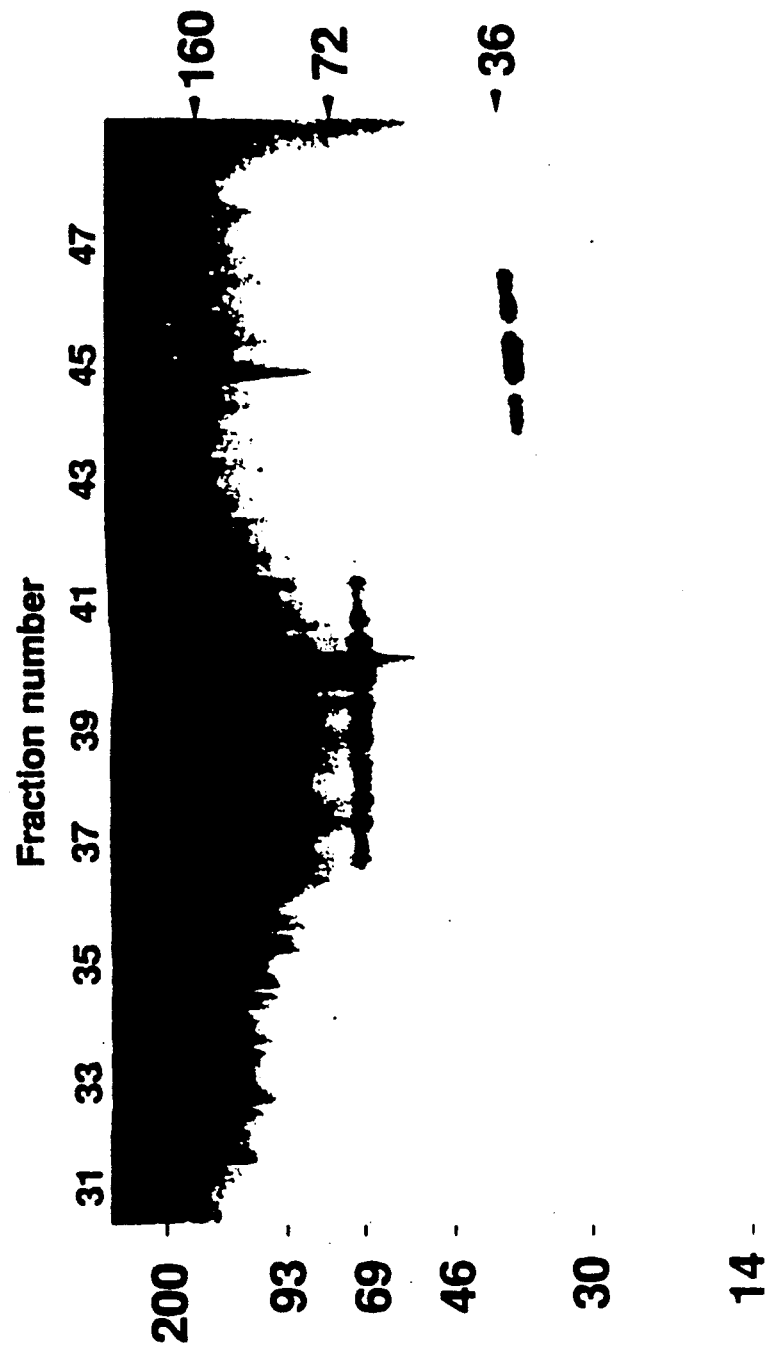
FIG. 9 is an SDS-gel analysis of various fractions obtained from Superose 12 chromatography.

Individual fractions 31-48 were then lyophilized and analyzed in 10 ul aliquots, using SDS-PAGE under non reducing conditions followed by silver staining. These results are shown in FIG. 9. They show that the 160 kd component eluted in a broad peak through fractions 32-42, while a 72 kd component eluted in fractions 37-40, and the 36 kd component in fractions 44-47. This last material was apparently homogeneous, and further analysis under reducing conditions showed a 40 kd fraction. These results indicate that this material is a single chain polypeptide, probably containing intrachain disulphide bonds. The absorbance values at 280 nm in FIG. 8 suggest that about 12 ug of this 40 kd molecule can be purified from 10 kg of tissue.

Example 11

Figure 10:
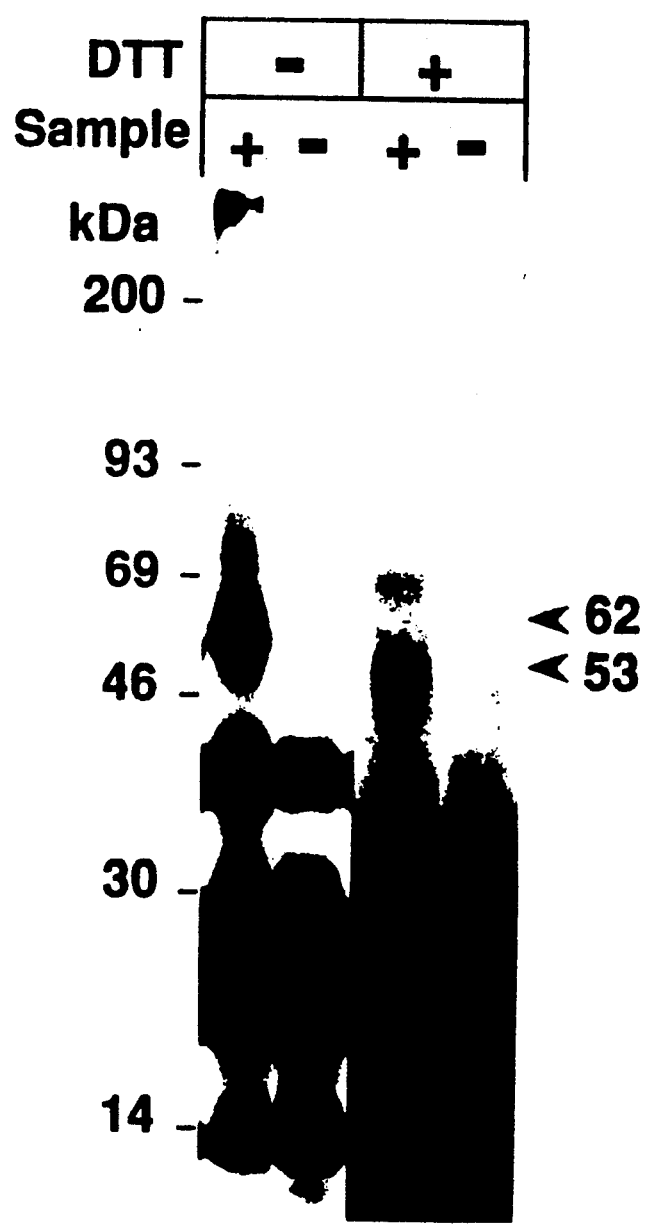
FIG. 10 shows analysis of the pure 40 kd component of the analysis, using $^{125}$-TGF-β1 affinity cross linking experiments

The 40 kd molecule was analyzed to test its binding to TGF-β1, using the affinity cross-linking protocols set forth supra. FIG. 10 shows that this experiment yielded a 62 kd complex under non-reducing conditions, and a 53 kd complex when 10 mM of DTT are present. If the molecular mass of TGF-β1 under non-reducing and reducing conditions are subtracted (25 kd, 12.5 kd), the resulting figure is 40 kd.

Figure 11:
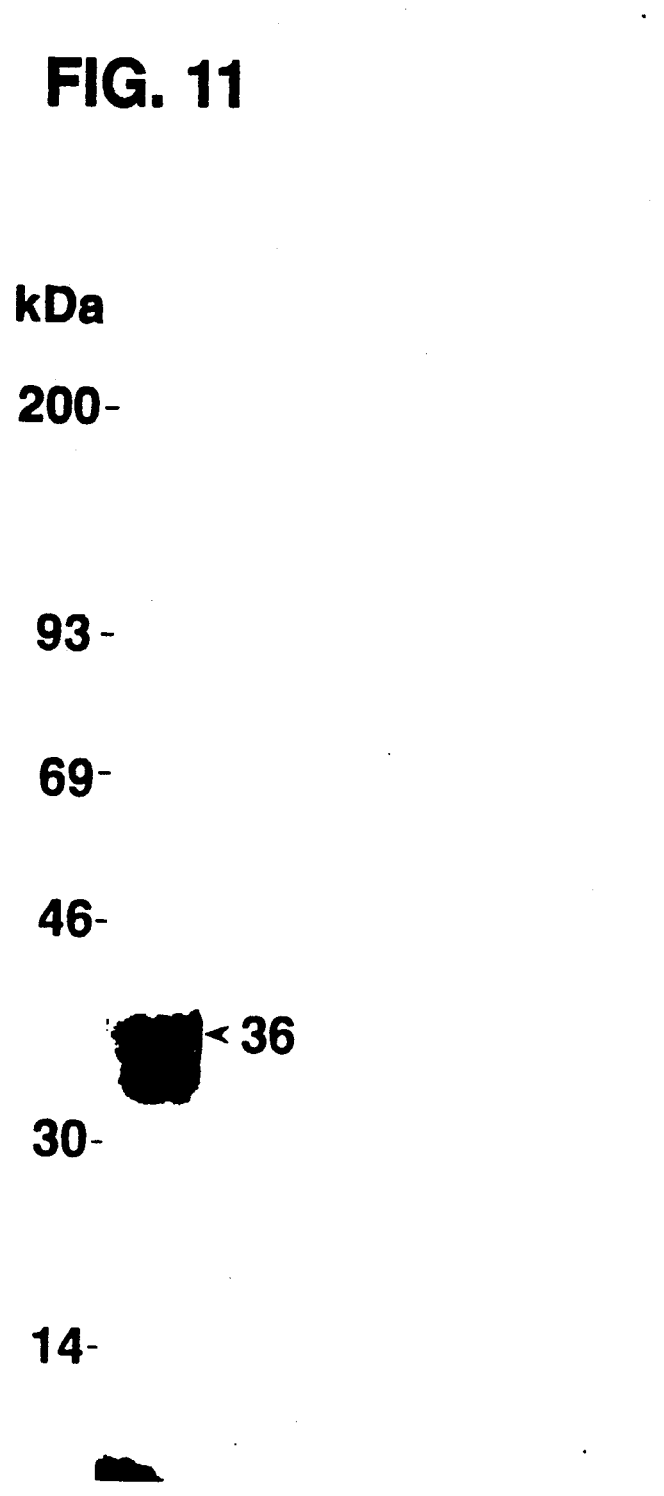

Similarly, when "in-gel" binding under non-reducing conditions was carried out, a labeled band is found at 36 kd, as shown in FIG. 11. This is the expected value, and the results prove that the substantially pure receptor like binding protein for TGF-β1 having a molecular mass of 36–40 kd does bind the molecule when in homogeneous form.

Example 12

The initial purification work, as per Example 1, used a wheat germ agglutinin column, so it cannot be ruled out that the materials of interest are glycoproteins. To that end, the molecules of the invention are described as "protein containing" because they definitely contain a protein component, and may be glycoproteins. Analysis of the homogeneous 40 kd component using endoglycosidase F, using SDS PAGE, silver staining and reducing conditions yielded a 35 kd product, so the molecules may be glycoproteins.

Example 13

Tryptic digestion of the 40 kd material has revealed some amino acid data. The following sequences have been identified:

(Tyr) Leu Gly Gly Ser Xaa Gly Ser Phe Ala
(SEQ ID NO: 1)
Val (Asp) Leu Val (Asp) Phe Glu Gly Asn His Gln Phe Ala
(SEQ ID NO: 2)
Val Val Gly Leu Glu Gly Ser Asp Lys Leu Ser Ile Leu Arg
(SEQ ID NO: 3)
Val Phe Gly Ser Gln Leu Gly Glu
(SEQ ID NO: 4)

where Xaa is hydroxyproline, and a bracketed amino acid means the determination is tentative. The peptide represented by SEQ ID NO: 3 has been used to prepare antiserum which specifically binds to glycoproteins.

The foregoing experiments demonstrate the existence of several receptor like binding proteins for TGF-β1. The term "receptor like" is used to distinguish these molecules generically from other molecules which have been referred to as "TGF-β1 binding proteins". The previously described molecules are substances which are complexed to the TGF-β1 molecule intracellularly and appear to be necessary to permit extracellular passage of the TGF-β1. In contrast, there was no evidence of the molecules of this invention being complexed to TGG-β1 when isolated. As such, they show "receptor like" properties in that they bind to and remove TGF-β1 from solution, but "receptor" is generally used to refer to a membrane bound material which is involved in reception of the target molecule. There is no evidence to link the described and claimed molecules of the invention to such a role, thus they are referred to as "receptor-like" rather than receptors.

The molecular mass determinations of the molecules, especially under reducing conditions (40, 80 and 160 kd), at first appear to suggest that these are related as mono-, di- and tetramer structures; however, this assumption is rebutted because the larger molecules resist reduction with 10 mM DTT in SDS at 95° C. for three minutes, a rather uncommon phenomenon for polypeptides with more than one chain.

The molecules appear to be glycoproteins based upon their ability to bind to wheat germ agglutinin columns, and the size reduction of the 40 kd molecule following endoglycosidase treatment.

The three molecules do not appear to have proteoglycan structures and are, therefore, clearly distinct from type III TGF-β receptor, which is a proteoglycan and is referred to as "betaglycan". Additional comparison to, e.g., decorin (Yamaguchi et al., Nature 346: 281–284 (1990)); α2 macroglobulin (O'Connor-McCourt, et al., J. Biol. Chem. 262; 14090–14099 (1987)); and type IV collagen (Paralker et al., DeV. Biol. 143: 303–308 (1991)), are not warranted because all of these molecules have size and subunit compositions different from the molecules described herein, and are secreted molecules, unlike those described and claimed herein.

The ability of these substantially pure receptor like TGF-β1 binding glycoproteins to bind TGF-β1 renders them useful in a number of ways. As indicated by the foregoing experiments, all three molecules bound to TGF-β1 on a column. As such, each can be used as a "probe" to detect TGF-β1 in a sample. Contact of the sample with the purified glycoprotein, followed by analysis for binding provides an assay method for TGF-β1. In addition, the ability of the glycoproteins to bind TGF-β1 makes them useful as therapeutic agents for preventing the binding of TGF-β1 to a cell with an actual receptor, thereby inhibiting the effect of the TGF-β1 if a sufficient amount of the glycoprotein is added. Other uses for the materials, such as an immunogen for production of antibodies, will be clear to the artisan and need not be set forth here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Substantially pure, membrane derived receptor like transforming growth factor β1 binding molecule, characterized by a molecular weight of from 35 to 40 kd as determined by SDS-PAGE.

2. Method for identifying transforming growth factor β1 binding protein in a sample, comprising contacting said sample with the substantially pure, receptor like binding molecule of claim 1 and determining binding to said binding molecule as a determination of transforming growth factor 1 in said sample.

3. The substantially pure, membrane derived receptor like transforming growth factor β1 binding molecule of claim 1, comprising the amino acid sequence of SEQ ID NO: 2.

4. The substantially pure, membrane derived receptor like transforming growth factor β1 binding molecule of claim 1, comprising the amino acid sequence of SEQ ID NO: 3.

5. The substantially pure, membrane derived receptor like transforming growth factor β1 binding molecule of claim 1, comprising the amino acid sequence of SEQ ID NO: 4.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 10 amino acids (B) TYPE: amino acids
        (D) TOPOLOGY: linear (ii) MOLECULE TYPE: protein (xi) SEQUENCE DESCRIPTION: SEQ ID NO: 1:

Tyr Leu Gly Gly Ser Xaa Gly Ser Phe Ala
                  5                    10

(2) INFORMATION FOR SEQ ID NO: 2:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO: 2:

Val Asp Leu Val Asp Phe Glu Gly Asn His Gln Phe Ala
                  5                    10

(2) INFORMATION FOR SEQ ID NO: 3:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO: 3:

Val Val Gly Leu Glu Gly Ser Asp Lys Leu Ser Ile Leu Arg
                  5                    10

(2) INFORMATION FOR SEQ ID NO: 4:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 4:

Val Phe Gly Ser Gln Leu Gly Glu
                  5